US006849092B2

(12) United States Patent
Van Dyke et al.

(10) Patent No.: US 6,849,092 B2
(45) Date of Patent: Feb. 1, 2005

(54) IMPLANTABLE PROSTHETIC OR TISSUE EXPANDING DEVICE

(75) Inventors: Mark E. Van Dyke, Fair Oaks Ranch, TX (US); Cheryl R. Blanchard, Warsaw, IN (US); Scott F. Timmons, San Antonio, TX (US); Arlene J. Siller-Jackson, Helotes, TX (US); Robert A. Smith, Jackson, MS (US)

(73) Assignee: Keraplast Technologies, Ltd., San Antonio, TX (US)

( * ) Notice: Subject to any disclaimer, the term of this patent is extended or adjusted under 35 U.S.C. 154(b) by 200 days.

(21) Appl. No.: 09/802,113

(22) Filed: Mar. 8, 2001

(65) Prior Publication Data

US 2001/0032019 A1 Oct. 18, 2001

Related U.S. Application Data

(63) Continuation of application No. 09/394,783, filed on Sep. 13, 1999, now Pat. No. 6,371,984.

(51) Int. Cl.[7] .................................................. A61F 2/44
(52) U.S. Cl. .................................. 623/17.12; 623/17.16
(58) Field of Search ........................... 623/17.11–17.16

(56) References Cited

U.S. PATENT DOCUMENTS

| | | | |
|---|---|---|---|
| 922,692 A | 5/1909 | Goldsmith | |
| 926,999 A | 7/1909 | Neuberg | |
| 960,914 A | 6/1910 | Heinemann | |
| 1,214,299 A | 1/1917 | Grosvenor et al. | |
| 2,434,688 A | 1/1948 | Evans | 18/47.5 |
| 2,445,028 A | 7/1948 | Jones et al. | 106/155 |
| 2,517,572 A | 8/1950 | Jones et al. | 106/155 |
| 2,814,851 A | 12/1957 | Hervey | 28/82 |
| 3,033,755 A | 5/1962 | Jacobi et al. | 167/90 |
| 3,642,498 A | 2/1972 | Anker | 99/166 |
| 3,655,416 A | 4/1972 | Vinson et al. | 106/155 |
| 3,867,728 A | 2/1975 | Stubstad et al. | 3/1 |
| 3,875,595 A | 4/1975 | Froning | 3/1 |
| 3,987,497 A | 10/1976 | Stoy et al. | 3/1 |
| 4,021,382 A | 5/1977 | Stoy et al. | 260/2.5 M |
| 4,026,296 A | 5/1977 | Stoy et al. | 128/349 B |
| 4,060,081 A | 11/1977 | Yannas et al. | 128/156 |
| 4,107,121 A | 8/1978 | Stoy | 260/29.6 AB |
| 4,123,406 A | 10/1978 | Stoy et al. | 260/29.6 AN |
| 4,135,942 A | 1/1979 | Kikkawa | 106/155 |
| 4,172,823 A | 10/1979 | Stoy et al. | 260/29.6 AN |
| 4,178,361 A | 12/1979 | Cohen et al. | 424/22 |
| 4,183,884 A | 1/1980 | Wichterle et al. | 264/41 |
| 4,228,056 A | 10/1980 | Stoy | 260/29.6 AN |
| 4,309,777 A | 1/1982 | Patil | 3/1.91 |
| 4,349,921 A | 9/1982 | Kuntz | 3/1 |
| 4,357,274 A | 11/1982 | Werner | 260/123 |
| 4,369,037 A | 1/1983 | Matsunaga et al. | 8/127.51 |
| 4,423,032 A | 12/1983 | Abe et al. | 424/70 |
| 4,439,417 A | 3/1984 | Matsunaga et al. | 424/70 |
| 4,485,097 A | 11/1984 | Bell | 424/95 |
| 4,495,173 A | 1/1985 | Matsunaga et al. | 424/70 |
| 4,570,629 A | 2/1986 | Widra | 128/156 |
| 4,685,447 A | 8/1987 | Iversen et al. | 128/1 R |
| 4,714,469 A | 12/1987 | Kenna | 623/17 |
| 4,751,074 A | 6/1988 | Matsunaga et al. | 424/70 |
| 4,766,005 A | 8/1988 | Montgomery et al. | 427/4 |
| 4,772,287 A | 9/1988 | Ray et al. | 623/17 |
| 4,837,379 A | 6/1989 | Weinberg | 424/101 |
| 4,839,168 A | 6/1989 | Abe et al. | 424/74 |
| 4,895,722 A | 1/1990 | Abe et al. | 424/71 |
| 4,904,260 A | 2/1990 | Ray et al. | 623/17 |
| 4,904,261 A | 2/1990 | Dove et al. | 623/17 |
| 4,911,718 A | 3/1990 | Lee et al. | 623/17 |
| 4,932,969 A | 6/1990 | Frey et al. | 623/17 |
| 4,936,848 A | 6/1990 | Bagby | 623/17 |
| 4,946,378 A | 8/1990 | Hirayama et al. | 623/17 |
| 4,959,213 A | 9/1990 | Brod et al. | 514/21 |

(List continued on next page.)

FOREIGN PATENT DOCUMENTS

| | | |
|---|---|---|
| CN | 1056986 A | 12/1991 |
| DE | 531446 | 1/1941 |
| DE | 3922203 C1 | 10/1990 |
| DE | 4222763 A1 | 1/1994 |
| EP | 0454600 A | 10/1991 |
| EP | 0 454 600 A1 | 10/1991 |

(List continued on next page.)

OTHER PUBLICATIONS

Wake, et al., "Dynamics of Fibrovascular Tissue Ingrowth in Hydrogel Foams," Cell Transplantation 4(3), 275–79, 1995.
Southwest Research Institute Annual Report, 17–18, 21, 1997.
Plant, et al., "Axonal growth within poly (2–hydroxyethyl methacrylate) sponges infiltrated with Schwann cells and implanted into the lesioned rat optic tract," Brain Research, 671, 119–30, 1995.
Technology Today, 16(3):9, 1995.

(List continued on next page.)

*Primary Examiner*—Corrine McDermott
*Assistant Examiner*—Thomas Barrett
(74) *Attorney, Agent, or Firm*—Vinson & Elkins L.L.P.

(57) ABSTRACT

A keratin hydrogel-filled implantable prosthetic device. One device is a breast implant for augmenting or reconstructing a human breast including an envelope containing a keratin hydrogel. One keratin hydrogel is formed from a solid precursor which forms a keratin hydrogel upon addition of water. One source of keratin is human hair. In one method, an envelope suitable for implantation and a solid keratin hydrogel precursor are provided. The solid can be in fibrous or powder form. The solid precursor can be inserted into the envelope interior. A small incision near the breast can be made and the envelope inserted into the incision. After insertion, water can be injected into the envelope interior, preferably through the incision and through a self-sealing port in the envelope. In one method, the implant is provided as a kit, with the envelope and keratin hydrogel provided. The hydrogel can be injected into the envelope either before or after insertion into the breast area. One kit has a powdered, keratin hydrogel precursor disposed within the envelope interior, awaiting the addition of water, preferably after insertion of the implant into the body.

29 Claims, No Drawings

U.S. PATENT DOCUMENTS

| | | | |
|---|---|---|---|
| 4,969,888 A | 11/1990 | Scholten et al. | 606/94 |
| 5,035,716 A | 7/1991 | Downey | 623/17 |
| 5,047,055 A | 9/1991 | Bao et al. | 623/17 |
| 5,047,249 A | 9/1991 | Rothman et al. | 424/543 |
| 5,059,193 A | 10/1991 | Kuslich | 606/61 |
| 5,123,926 A | 6/1992 | Pisharodi | 623/17 |
| 5,134,031 A | 7/1992 | Kagechi et al. | 428/373 |
| 5,192,326 A | 3/1993 | Bao et al. | 623/17 |
| 5,258,043 A | 11/1993 | Stone | 623/66 |
| 5,276,138 A | 1/1994 | Yamada et al. | 530/357 |
| 5,292,362 A | 3/1994 | Bass et al. | 106/124 |
| 5,304,378 A | 4/1994 | Koga et al. | 424/445 |
| 5,306,309 A | 4/1994 | Wagner et al. | 623/17 |
| 5,320,796 A | 6/1994 | Harashima et al. | 264/349 |
| 5,324,775 A | 6/1994 | Rhee et al. | 525/54.2 |
| 5,358,935 A | 10/1994 | Smith et al. | 514/21 |
| 5,390,683 A | 2/1995 | Pisharodi | 128/898 |
| 5,443,514 A | 8/1995 | Steffee | 623/17 |
| 5,458,643 A | 10/1995 | Oka et al. | 623/18 |
| 5,474,770 A | 12/1995 | Broly et al. | 424/94.64 |
| 5,480,430 A | 1/1996 | Carlisle et al. | 623/8 |
| 5,505,732 A | 4/1996 | Michelson | 606/61 |
| 5,514,180 A | 5/1996 | Heggeness et al. | 623/17 |
| 5,522,898 A | 6/1996 | Bao | 623/17 |
| 5,534,028 A | 7/1996 | Bao et al. | 623/17 |
| 5,534,029 A | 7/1996 | Shima | 623/17 |
| 5,549,672 A | 8/1996 | Maddock et al. | 623/8 |
| 5,549,679 A | 8/1996 | Kuslich | 623/17 |
| 5,552,452 A | 9/1996 | Khadem et al. | 522/63 |
| 5,561,107 A | 10/1996 | Jaynes et al. | 514/12 |
| 5,562,736 A | 10/1996 | Ray et al. | 623/17 |
| 5,589,451 A | 12/1996 | Wilson | 512/2 |
| 5,632,774 A | 5/1997 | Babian | 623/8 |
| 5,634,945 A | 6/1997 | Pernia et al. | 623/11 |
| 5,645,597 A | 7/1997 | Krapiva | 623/17 |
| 5,653,984 A | 8/1997 | Fodor et al. | 424/195.1 |
| 5,660,857 A | 8/1997 | Haynes et al. | 424/450 |
| 5,674,295 A | 10/1997 | Ray et al. | 623/17 |
| 5,676,702 A | 10/1997 | Ratron | 623/17 |
| 5,679,819 A | 10/1997 | Jones et al. | 556/418 |
| 5,694,946 A | 12/1997 | Tenerz et al. | 128/748 |
| 5,702,455 A | 12/1997 | Saggar | 623/17 |
| 5,703,047 A | 12/1997 | Wilson | 514/12 |
| 5,705,780 A | 1/1998 | Bao | 204/157.15 |
| 5,707,805 A | 1/1998 | Rubin et al. | 435/6 |
| 5,712,252 A | 1/1998 | Smith | 514/21 |
| 5,716,404 A | 2/1998 | Vacanti et al. | 623/8 |
| 5,716,415 A | 2/1998 | Steffee | 623/17 |
| 5,723,331 A | 3/1998 | Tubo et al. | 435/366 |
| 5,725,582 A | 3/1998 | Bevan et al. | 623/17 |
| 5,728,405 A | 3/1998 | McDonnell | 424/682 |
| 5,755,814 A | 5/1998 | Berg et al. | 623/66 |
| 5,763,583 A | 6/1998 | Arai et al. | 530/353 |
| 5,766,252 A | 6/1998 | Henry et al. | 623/17 |
| 5,782,831 A | 7/1998 | Sherman et al. | 606/61 |
| 5,785,964 A | 7/1998 | Naughton et al. | 424/93.21 |
| 5,786,217 A | 7/1998 | Tubo et al. | 435/402 |
| 5,791,352 A | 8/1998 | Reich et al. | 128/898 |
| 5,792,090 A | 8/1998 | Ladin | 602/48 |
| 5,800,549 A | 9/1998 | Bao et al. | 623/17 |
| 5,814,605 A | 9/1998 | Pierce et al. | 514/12 |
| 5,824,093 A | 10/1998 | Ray et al. | 623/17 |
| 5,824,113 A | 10/1998 | Hogo | 8/128.3 |
| 5,824,331 A | 10/1998 | Usala | 424/424 |
| 5,827,328 A | 10/1998 | Buttermann | 623/17 |
| 5,842,477 A | 12/1998 | Naughton et al. | 128/898 |
| 5,854,207 A | 12/1998 | Lee et al. | 514/2 |
| 5,865,846 A | 2/1999 | Bryan et al. | 623/17 |
| 5,874,500 A * | 2/1999 | Rhee et al. | 525/54.1 |
| 5,888,224 A | 3/1999 | Beckers et al. | 623/17 |
| 5,914,265 A | 6/1999 | Roop et al. | 435/320.1 |
| 5,916,565 A | 6/1999 | Rose et al. | 424/195.1 |
| 5,916,870 A | 6/1999 | Lee et al. | 514/2 |
| 5,932,552 A | 8/1999 | Blanchard et al. | 514/21 |
| 5,948,428 A | 9/1999 | Lee et al. | 424/426 |
| 5,948,432 A | 9/1999 | Timmons et al. | 424/443 |
| 5,955,083 A | 9/1999 | Bonte et al. | 424/195.1 |
| 5,972,031 A | 10/1999 | Biedermann et al. | 623/17 |
| 5,976,186 A | 11/1999 | Bao et al. | 623/17 |
| 6,004,323 A | 12/1999 | Park et al. | 606/61 |
| 6,008,013 A | 12/1999 | Reynolds | 435/69.1 |
| 6,022,376 A * | 2/2000 | Assell et al. | 623/17.16 |
| 6,063,061 A | 5/2000 | Wallace et al. | 604/181 |
| 6,063,378 A | 5/2000 | Nohara et al. | 424/94.61 |
| 6,077,987 A | 6/2000 | Breitbart et al. | 623/11 |
| 6,093,205 A | 7/2000 | McLeod et al. | 623/17 |
| 6,105,581 A | 8/2000 | Eggers et al. | 128/898 |
| 6,110,208 A | 8/2000 | Soranzo et al. | 623/15 |
| 6,110,210 A | 8/2000 | Norton et al. | 623/17.16 |
| 6,110,487 A | 8/2000 | Timmons et al. | 424/443 |
| 6,110,891 A | 8/2000 | Pusztai et al. | 514/8 |
| 6,113,639 A | 9/2000 | Ray et al. | 623/11 |
| 6,124,265 A | 9/2000 | Timmons et al. | 514/21 |
| 6,124,273 A | 9/2000 | Drohan et al. | 514/55 |
| 6,274,163 B1 | 8/2001 | Blanchard et al. | 424/443 |
| 6,306,177 B1 * | 10/2001 | Felt et al. | 623/23.6 |

FOREIGN PATENT DOCUMENTS

| | | |
|---|---|---|
| EP | 0468797 B1 | 12/1995 |
| GB | 531446 | 1/1941 |
| JP | S55-187190 | 12/1980 |
| JP | 56129035 | 10/1981 |
| JP | SHO 54-124043 | 2/1982 |
| JP | SHO59-155248 | 9/1984 |
| JP | SHO 60-220068 | 11/1985 |
| JP | 1988-202582 | 8/1988 |
| JP | 03011099 A | 1/1991 |
| JP | 04091138 A | 3/1992 |
| JP | 04091138 A2 | 3/1992 |
| JP | 1992-174659 | 5/1992 |
| JP | HEI 4-189833 | 7/1992 |
| JP | 5285374 | 11/1993 |
| JP | 5285375 | 11/1993 |
| JP | 1993285374 A | 11/1993 |
| JP | 1993285375 A | 11/1993 |
| JP | 6116300 | 4/1994 |
| JP | 1994100600 A | 4/1994 |
| JP | 1994116300 A | 4/1994 |
| JP | HEI 6-293631 | 10/1994 |
| JP | 06336499 A | 12/1994 |
| JP | 6336499 | 12/1994 |
| JP | 1998291999 A | 11/1998 |
| JP | 1998337466 A | 12/1998 |
| JP | 2001087754 | 4/2001 |
| WO | WO 91/02538 | 3/1991 |
| WO | WO 98/08550 | 3/1998 |
| WO | WO 99/26595 * | 6/1999 |
| WO | WO 03/011894 A1 | 2/2003 |
| WO | WO 03/018673 A1 | 3/2003 |

OTHER PUBLICATIONS

Rhodes, et al., "Characteristics of the alpha–keratose fraction of hair inducing ascosporogensis in *Nannizia grubyia*," Mycopathologia et Mycologia Applicata, 33, 345–48, 1967.

Chargaff, et al., "Techniques for the demonstration by chromatography of nitrogenous lipide constituents, sulfur–containing amino acids, and reducing sugars," *J. Biol. Chem.*, 175(1):67–71, 1948.

Yamauchi, et al., "Cultivation of fibroblast cells on keratin–coated substrata," Polymers for Tissue Engineering, 329–40, 1998.

Thomas et al., "Isolation of microfibrillar proteins of wool in disulfide form," Melliand Texiberichte, 65(3):20809, 1984.

van de Löcht, "Reconstitution of microfibrils from wool and filaments from epidermis proteins," Melliand Textiberichte, 10:780–6, 1987.

Yoshioka et al., "Cosmetic base," unexamined Japanese Patent Application No. 3–223207, Oct. 2, 1991.

Yoshioka et al., "Water–soluble hair dressing agent," unexamined Japanese Patent Application No. 8–157342, Jun. 18, 1996.

Hyuku et al., "Novel amino acid silicone polymer, production thereof, cosmetic particles surface treated with the polymer, and cosmetic containing said particles," unexamined Japanese Patent Application No. 2001–114647, Apr. 24, 2001.

Ito et al., "Biocompatibility of denatured wool keratin," 39:4, 249–256, Apr. 1982.

Yamauchi, "The development of keratin: characteristics of polymer films," Fragrance J, 21(5), 62–7, 1993.

Sauk et al., "Reconstitution of cytokeratin filaments in vitro: further evidence for the role of nonhelical peptides in filament assembly," The Journal of Cell Biology, 99, 1590–1597, Nov. 1984.

Weber et al., "The structural relation between intermediate filament proteins in living cells and the α–keratins of sheep wool," The EMBO Journal, 1:10, 1155–1160, 1982.

Hanukoglu et al., "The cDNA sequence of a human epidermal keratin: divergence of sequence but conservation of structure among intermediate filament proteins," Cell, 31, 243–252, Nov. 1982.

Fraser et al., "Intermediate filaments in α–keratins," Proc. Natl. Acad. Sci. USA, 83, 1179–1183, Mar. 1986.

Jones, "Studies on microfibrils from α–keratin," Biochimica et Biophysica Acta, 446, 515–524, Received Apr. 5th, 1976.

Zackroff, et al., "In vitro assembly of intermediate filaments from baby hamster kidney (BHK–21) cells," Proc. Natl. Acad. Sci. USA, 76:12, 6226–6230, Dec. 1979.

Mack, et al., "Solid–state NMR studies of the dynamics and structure of mouse keratin intermediate filaments," Biochemistry, 27, 5418–5426, 1988.

Skerrow, et al., "Epidermal α–keratin is neutral–buffer–soluble and forms intermediate filaments under physiological conditions in vitro," Biochimica et Biophysica, 915, 125–131, 1987.

Kvedar, et al., "Cytokeratins of the bovine hoof: classification and studies on expression," Biochimica et Biophysica Acta, 884, 462–473, 1986.

Moll, et al., "The catalog of human cytokeratins: patterns of expression in normal epithelia, tumors and cultured cells," Cell, 31, 11–24, Nov. 1982.

Iwatsuki, et al., "Comparative studies on naturally occurring antikeratin antibodies in human sera," The Journal of Investigative Dermatology, 87:2, 179–184, Aug. 1986.

Lambré, et al., "An enzyme immunoassay for auto–antibodies to keratin in normal human serum and in pleural fluids from patients with various malignant or non–malignant lung diseases," J. Clin. Lab. Immunol., 20, 171–176, 1986.

Stokes, et al., "Passage of water and electrolytes through natural and artificial keratin membranes," Desalination, 42, 321–328, 1982.

Dedeurwaerder, et al., "Selective extraction of a protein fraction from wool keratin," Nature, 265, 48–49, and 274–276, Jan. 20, 1977.

Brunner, et al., "Fractionation of tyrosine–rich proteins from oxidized wool by ion–exchange chromatography and preparative electrophoresis," Eur. J. Biochem., 32, 350–355, 1973.

Mies, et al., "Chromatographic and electrophoretic investigations of the properties of unprotected low–sulphur wool kerateins," Journal of Chromatography, 405, 365–370, 1987.

Katsuumi, et al., "Two–dimensional electrophoretic analysis of human hair keratins, especially hair matrix proteins," Arch. Dermatol. Res., 281, 495–501, 1989.

Horn, et al., "Relative molecular masses of reduced wool keratin polypeptides," Biochem Soc Trans, 14, 333–334, 1986.

Harrap, et al., "Species differences in the proteins of feathers," Comp. Biochem. Physiol., 20, 449–460, 1967.

Harrap, et al., "Soluble derivatives of feather keratin," Biochem. J., 92, 8–18, 1964.

Yoshimizu, et al., "$^{13}$C CP/MAS NMR study of the conformation of stretched or heated low–sulfur keratin protein films," Macromolecules, 24, 862–866, 1991.

Schaller, et al., "Membranes prepared from keratin–polyacrylonitrile graft copolymers," Journal of Applied Polymer Science, 25, 783–794, 1980.

Weiss, et al., "The use of monoclonal antibody to keratin in human epidermal disease: alterations in immunohistochemical staining pattern," The Journal of Investigative Dermatology, 81, 224–230, 1983.

Starger, et al., "Biochemical and immunological analysis of rapidly purified 10–nm filaments from baby hamster kidney (BHK–21) cells," J. Cell Biology, 78, 93–109, 1978.

Noishiki, et al., "Application of denatured wool keratin derivatives to an antithrombogenic biomaterial—vascular graft coated with a heparinized keratin derivative—," Inst. Thermal Spring Res. Okayama Univ., 39:4, 221–227, 1982.

Dale, "Keratin and other coatings for pills," Pharm. J., 129, 494–495, 1932, Abstract.

Schrooyen, et al., "Biodegradable films from selectively modified feather keratin dispersions," Polymer Preprints (American Chemical Society, Division of Polymer Chemistry), 39(2), 160, 1998, Abstract.

Schrooyen, et al., "Polymer films from chicken feather keratin," Book of Abstracts, 216th ACS National Meeting, Boston, Aug. 23–27, 1998, Abstract.

Kikkawa, et al., "Solubilization of keratin. 6. Solubilization of feather keratin by oxidation with performic acid," Hikaku Kagaku, 20(3), 151–162, 1974, Abstract.

Matsunaga, et al., "Studies on the chemical property of human hair keratin. Part 1. Fractionation and amino acid composition of human hair keratin solubilized by performic acid oxidation," Hikaku Kagaku, 27(1), 21–29, 1981, Abstract.

Noishiki et al., "Application of denatured wool keratin derivatives to an antithrombogenic biomaterial. Vascular graft coated with a heparinized keratin derivative," Kobunshi Ronbunshu, 39(4), 221–227, 1982, Abstract.

Ito, et al., "Biocompatibility of denatured keratins from wool," Kobunshi Ronbunshu, 39(4), 249–256, 1982, Abstract.

Gillespie,, et al., "Amino acid composition of a sulphur–rich protein from wool," *Biochimica et Biophysica Acta*, 39, 538–539, 1960.

Gough, et al., "Amino acid sequences of α–helical segments from S–carboxymethylkerateine–A. Complete sequence of a type–I segment," *Biochem. J.*, 173, 373–385, 1978.

Elleman, et al., "Amino acid sequences of α–helical segments from S–carboxymethylkerateine–A. Statistical analysis," *Biochem. J.*, 173, 387–391, 1978.

Hogg, et al., "Amino acid sequences of α–helical segments from S–carboxymethylkerateine–A. Tryptic and chymotryptic peptides from type–II segment," *Biochem. J.*, 173, 353–363, 1978.

Earland, et al., "Studies on the structure of keratin. II. The amino acid content of fractions isolated from oxidized wool," *Biochemica et Biophysica Acta*, 22, 405–411, 1956.

Crewther, et al., "Amino acid sequences of α–helical segments from S–carboxymethylkerateine–A. Complete sequence of a type–II segment," *Biochem. J.*, 173, 365–371, 1978.

Fraser, et al., "Microscopic observations of the alkaline–thioglycollate extraction of wool," *Biochimica et Biophysica Acta*, 22, 484–485, 1953.

Gillespie, et al., "Preparation of an electrophoretically homogeneous keratin derivative from wool," *Biochimica et Biophysica Acta*, 12, 481–483, 1953.

Blagrove, et al., "The electrophoresis of the high–tyrosine proteins of keratins on cellulose acetate strips," *Comp. Biochem. Physiol.*, 50B, 571–572, 1975.

Frenkel, et al., "The isolation and properties of a tyrosine–rich protein from wool: component 0.62," *Eur. J. Biochem.*, 34, 112–119, 1973.

Marshall, et al., "Successful isoelectric focusing of wool low–sulphur proteins," *Journal of Chromatography*, 172, 351–356, 1979.

Marshall, "Characterization of the proteins of human hair and nail by electrophoresis," *The Journal of Investigative Dermatology*, 80:6, 519–524, 1983.

Lindley, et al., "Occurrence of the cys–cys sequence in keratins," *J. Mol. Biol.*, 30, 63–67, 1967.

Marshall, "Genetic variation in the proteins of human nail," *The Journal of Investigative Dermatology*, 75:3, 264–269, 1980.

Goddard, et al., "A study on keratin," *J. Bio. Chem.*, 106, 605–614, 1934.

Dowling, et al., "Isolation of components from the low–sulphur proteins of wool by fractional precipitation," *Preparative Biochemistry*, 4(3), 203–226, 1974.

Crewther, et al., "Reduction of S–carboxymethylcysteine and methionine with sodium in liquid ammonia," *Biochimica et Biophysica Acta*, 194, 606–609, 1969.

Gillespie, "The isolation from wool of a readily extractable protein of low sulphur content," *Biochimica et Biophysica Acta*, 27, 225–226, 1958.

Lindley, et al., "The reactivity of the disulphide bonds of wool," *Biochem. J.*, 139, 515–523, 1974.

Mitsui, et al., "Genes for a range of growth factors and cyclin–dependent kinase inhibitors are expressed by isolated human hair follicles," *British Journal of Dermatology*, 137(5), 693–698, 1997, Abstract.

Schörnig, et al., "Synthesis of nerve growth factor mRNA in cultures of developing mouse whisker pad, a peripheral target tissue of sensory trigeminal neurons," *The Journal of Cell Biology*, 120:6, 1471–1479, 1993.

Filshie, et al., "The fine structure of α–keratin," *J. Mol. Biol.*, 3, 784–786, 1961.

Filshie, et al., "An electron microscope study of the fine structure of feather keratin," *The Journal of Cell Biology*, 13, 1–2, 1962.

Crewther, et al., "Low–sulfur proteins from α–keratins. Interrelationships between their amino acid compositions, α–helix contents, and the supercontraction of the parent keratin," *Biopolymers*, 4, 905–916, 1966.

Bhatnagar, et al., "The conformance of the high–sulphur proteins of wool. I. The preparation and properties of a water–soluble metakeratin," *Int. J. Protein Research I*, 199–212, 1969.

Crewther, et al., "The preparation and properties of a helix–rich fraction obtained by partial proteolysis of low sulfur S–carboxymethylkerateine from wool," *The Journal of Biological Chemistry*, 242:19, 4310–4319, 1967.

Parry, et al., "Structure of α–keratin: structural implication of the amino acid sequences of the type I and type II chain segments," *J. Mol. Biol.*, 113, 449–454, 1977.

Suzuki, et al., "X–ray diffraction and infrared studies of an α–helical fragment from α–keratin," *J. Mol. Biol.*, 73, 275–278, 1973.

Bhatnagar, et al., "The conformation of the high–sulphur proteins of wool. II. Difference spectra of kerateine–B," *Int. J. Protein Research I*, 213–219, 1969.

Steinert, et al., "In vitro studies on the synthesis of guinea pig hair keratin proteins," *Biochimica et Biophysica Acta*, 312, 403–412, 1973.

Rogers, "Some observations on the proteins of the inner root sheath cells for hair follicles," *Biochimica et Biophysica Acta*, 29, 33–42, 1958.

Tachibana, et al., "Fabrication of wool keratin sponge scaffolds for long–term cell cultivation," *Journal of Biotechnology*, 93, 165–170, 2002.

Gillespie, "Proteins rich in glycine and tyrosine from keratins," *Comp. Biochem. Physiol.*, 41B, 723–734, 1972.

Fraser, et al., "Tyrosine–rich proteins in keratins," *Comp. Biochem. Physiol.*, 44B, 943–947, 1973.

Bendit, et al., "Communications to the Editor. The probably role and location of high–glycine–tyrosine proteins in the structure of keratins," *Biopolymers*, 17, 2743–2745, 1978.

Lindley, et al., "The preparation and properties of a group of proteins from the high–sulphur fraction of wool," *Biochem. J.*, 128:859–867, 1972.

Gillespie, et al., "Evidence of homology in a high–sulphur protein fraction (SCMK–B2) of wool and hair α–keratins," *Biochem. J.*, 110, 193–198, 1968.

Wormell, "Regenerated protein fibres from wool and casein," *The Journal of Textile Institute*, 18, T219–T224, 1948.

Harding, et al., "Formation of the $_e$–(γ–glutamyl) lysine cross–link in hair proteins. Investigation of transamidases in hair follicles," *Biochemistry*, 11:15, 2858–2863, 1972.

Powell, et al., "Control of feather keratin synthesis by the availability of keratin mRNA," *Biochemical and Biophysical Research Communications*, 68:4, 1263–1271, 1976.

Strüsmann, et al., "Specific radiolabeling of keratin proteins by amidination," *Journal of Chromatography*, 268, 306–310, 1983.

Lindley, et al., "Disulphide interchange reactions involving cyclocystine and their relevance to problems of α–keratin structure," *Biochem. J.*, 108, 701–703, 1968.

Damoglou, et al., "The hydrolysis by thermolysin of dipeptide derivatives that contain substituted cysteine," *Biochem. J.*, 123, 379–384, 1971.

Lennox, et al., "Photochemical degradation of keratins," *Photochemistry and Photobiology*, 9, 359–367, 1969.

Crewther, et al., "Preliminary Notes. The relation between the disulphide content of wool and the two–stage supercontraction of wool fibres in solutions of LiBr," *Biochimica et Biophysica Acta*, 46, 605–606, 1961.

Gillespie, et al., "A comparison of the proteins of normal and trichothiodystrophic human hair," *The Journal of Investigative Dermatology*, 80, 195–202, 1983.

Gillespie, et al., "Changes in the proteins of wool following treatment of sheep with epidermal growth factor," *The Journal of Investigative Dermatology*, 79:3, 197–200, 1982.

Gillespie, et al., "Changes in the matrix proteins of wool and mouse hair following the administration of depilatory compounds," *Aust. J. Biol. Sci.*, 33, 125–136, 1980.

Darskus, et al., "Breed and species differences in the hair proteins of four genera of caprini," *Aust. J. Biol. Sci.*, 24, 515–524, 1971.

Kemp, et al., "Differentiation of avian keratinocytes. Characterization and relationships of the keratin proteins of adult and embryonic feathers and scales," *Biochemistry*, 11:6, 969–975, 1972.

Gillespie, et al., "The diversity of keratins," *Comp. Biochem. Physiol.*, 47B, 339–346, 1974.

Fraser, et al., "Wool structure and biosynthesis," *Nature*, 261, 650–654, 1976.

Stenn, et al., editors, "The molecular and structural biology of hair," *Annals of the New York Academy of Sciences*, vol. 642, Title Page—31, 1991.

Reis, et al., "The utilization of abomasal supplements of proteins and amino acids by sheep with special reference to wool growth," *Aust. J. Biol., Sci.*, 25, 1057–1071, 1972.

Broad, et al., "The influence of sulphur–containing amino acids on the biosynthesis of high–sulphur wool proteins," *Aust. J. Biol. Sci.*, 23, 149–164, 1970.

Reis, "The influence of dietary protein and methionine on the sulphur content and growth rate of wool in milk–fed lambs," *Aust. J. Biol. Sci.*, 23, 193–200, 1970.

Downes, et al., "Metabolic fate of parenterally administered sulphur–containing amino acids in sheep and effects on growth and composition of wool," *Aust. J. Biol. Sci.*, 23, 1077–1088, 1970.

Reis, "The growth and compositon of wool.IV. The differential response of growth and of sulphur content of wool to the level of sulphur–containing amino acids given per abomasum," *Aust. J. Biol. Sci.*, 20, 809–825, 1967.

Reis, et al., "Effects of phenylalanine and analogues of methionine and phenylalinine on the composition of wool and mouse hair," *Aust. J. Biol. Sci.*, 38:2, 151–163.

Frenkel, et al., "Studies on the inhibition of synthesis of the tyrosine–rich proteins of wool," *Aust. J. Biol. Sci.*, 28, 331–338, 1975.

Frenkel, et al., "Factors influencing the biosynthesis of the tyrosine–rich proteins of wool," *Aust. J. Biol. Sci.*, 27, 31–38, 1974.

Reis, "The growth and composition of wool. III. Variations in the sulphur content of wool," *Aust. J. Biol. Sci.*, 18, 671–687, 1965.

Reis, et al., "The influence of abomasal and intravenous supplements of sulphur–containing amino acids on wool growth rate," *Aust. J. Biol. Sci.*, 26, 249–258, 1973.

Gillespie, et al., "A further study on the dietary–regulated biosynthesis of high–sulphur wool proteins," *Biochem. J.*, 112, 41–49, 1969.

Gillespie, et al., "The dietary–regulated biosynthesis of high–sulphur wool proteins," *Biochem. J.*, 98, 669–677, 1966.

Powell, et al., "Characterization of a gene encoding a cysteine–rich keratin associated protein synthesized late in rabbit hair follicle differentiation," *Differentiation*, 58, 277–232, 1995.

Powell, et al., "Cyclic hair–loss and regrowth in transgenic mice overexpressing an intermediate filament gene," *The EMBO Journal*, 9:5, 1485–1493, 1990.

Raphael, et al.,"Protein and amino acid composition of hair from mice carrying the naked (N) gene," *Genet. Res. Camb.*, 44:1, 29–38, 1984.

Frenkel, et al., "The keratin BIIIB gene family: isolation of cDNA clones and structure of a gene and a related pseudogene," *Genomics*, 4, 182–191, 1989.

Dowling, et al., "The primary structure of component 8c–1, a subunit protein of intermediate filaments in wool keratin," *Biochem. J.*, 236, 695–703, 1986.

Dowling, et al., "Secondary structure of component 8c–1 of α–keratin," *Biochem. J.*, 236, 705–712, 1986.

Kuczek, et al., "Sheep wool (glycine + tyrosine)–rich keratin genes," *Eur. J. Biochem.*, 166, 79–85, 1987.

Inagaki, et al., "Functionality of lamb wool keratin derivatives and a few characteristics of polymer materials for medical applications," *Chemical Research Institute, Kyoto University*.

Sakabe, et al., "Differential thermal analysis of component proteins from wool," *Sen–I Gakkaishi* 39(12): T–517–T–522 (1982).

"Biomaterial forefront. Keratin which can be extracted by a simple chemical technique," Kogyo Zairyo (Engineering Materials), 41:15, 106–109, 1993.

Kulkarni, "Further studies on the microfibrils from wool keratin. Part I: the isolation of microfibrils," *Text. Res. J.*, 46:11, 833–5, 1976, Abstract.

Edwards, "Chemical studies on powdered keratins," *The Journal of Biological Chemistry*, 154, 593–596, 1944.

* cited by examiner

IMPLANTABLE PROSTHETIC OR TISSUE EXPANDING DEVICE

PRIORITY AND CROSS REFERENCE TO CO-PENDING APPLICATIONS

The present application is a continuation of U.S. patent Ser. No. 09/394,783, U.S. Pat. No. 6,371,984 filed Sep. 13, 1999. This present application is also related to U.S. Pat. No. 6,270,791, filed Jun. 11, 1999, entitled SOLUBLE KERATIN PEPTIDE, and U.S. Pat. No. 6,316,598, filed Sep. 13, 1999, entitled WATER ABSORBENT KERATIN AND GEL FORMED THEREFROM.

FIELD OF THE INVENTION

The present invention is generally related to medical prostheses or implants for augmentation, tissue expansion or replacement of soft tissue, including breast implants. In particular, the present invention is related to implants filled with a keratin hydrogel.

BACKGROUND OF THE INVENTION

Breast augmentation and reconstruction through medical procedures has been performed by physicians for decades. Early attempts using filler materials alone, without an enclosing envelope, had less than optimal long-term effects on appearance and health. The use of silicone gel-filled silicone envelopes gave improved long-term appearance but has created concerns for manufacturers, surgeons and patients due to possible leakage of the silicone gel from the envelopes into the body. These concerns had the effect of removing silicone gel-filled breast implants from some markets, such as the United States. Saline-filled breast implants have been used in place of the silicone-filled implants. The use of saline has led to fewer concerns, but saline-filled silicone implants have been reported as having a less natural shape and consistency.

Another issue in the field of breast reconstruction and in the healing of open wounds is the use of tissue expanders. Tissue expanders typically include a bladder or envelope that will hold a liquid such as saline. The expander is placed over a wound, or may be implanted under tissue, such as under the muscles below a surgically removed breast. During use in breast reconstruction, a small amount of saline is added to the envelope periodically until the desired size is reached. By adding liquid slowly over a period of weeks or months, the covering tissue is allowed to expand to accommodate its size. Tissue expanders may also be used to cover an open wound and serve as a platform for the growth of new skin over the wound. Unfortunately, in order to change the volume of the tissue expander a needle must be inserted into the envelope, thus requiring penetration of the tissue and causing pain and an increased possibility of infection.

What would be desirable is a safe, non-toxic, non-antigenic material for use in implants that has a consistency more like that of the original human soft tissue. A further advantage would be an implant that can be implanted using potentially minimally invasive surgical procedures. What would be desirable is a tissue expander that is able to absorb fluid from the patient after implantation so that the expander could reach the desired size without repeated intrusive procedures.

SUMMARY OF THE INVENTION

The present disclosure addresses the shortcomings of the prior art by providing a safer, more natural appearing implant for augmenting or reconstructing the human breast or other tissue such as penile, testicular, gluteal, or facial tissue. Preferred implants include an outer envelope made of silicone or a biocompatible polymer and having an interior containing a keratin hydrogel. The hydrogel can be made from a keratinous material that is obtained from a biological source, especially keratin obtained from hair, feathers, hooves, feet, beaks, skin or nails of a mammal. The keratin is preferably obtained from hair, and more preferably from human hair. Human hair is especially desirable because of its ready availability as cuttings from barber and beauty shops, because human hair is likely to have less antigenicity in a human subject, and because hair can be harvested from the intended implant recipient. In certain embodiments implants include a hydrogel formed from hydrating a keratin material prepared as described in copending U.S. patent application Ser. No. 09/394,782, filed Sep. 13, 1999 and entitled "Water Absorbent Keratin and Gel Formed Therefrom," incorporated herein in its entirety by reference. In certain embodiments implants include a keratin hydrogel formed using an alternative method as described in U.S. Pat. No. 5,932,552 and U.S. Pat. No. 6,159,496 both incorporated herein in their entirety by reference.

In more detail, a keratin hydrogel for use in the prosthetic devices described herein may be formed by adding an aqueous solvent such as water to a hydratable keratin material. This hydratable material can be made by a first process beginning with providing a keratinous material including keratin having disulfide bonds and partially oxidizing the keratin disulfide bonds, such that sulfonic acid residues are formed. The sulfonic acid containing keratin material can subsequently be placed in a solvent containing cations, preferably monovalent cations. In certain preferred embodiments, a solution containing the oxidized keratin material is neutralized, or raised to a pH that is less acidic than the oxidation solution. Without limiting the patent to a particular mechanism, in certain embodiments, and depending on the solvent used, the pH may be raised to a level above the pKa of the sulfonic acid groups to obtain sulfonic acid groups in an anionic state, or having a negative charge. It is contemplated that anionic sulfonic acid groups may more easily form ionic associations or even ionic bonds with the cations. When a substantial part of the liquid is removed from the keratin/cationic solution, a salt or solid salt including the keratin and cations may be isolated. This solid is hydratable, highly absorbent, and forms a hydrogel upon re-hydration. The solid may be used in fibrous or powdered form, and adding water to the solid forms a viscoelastic hydrogel suitable for use as a prosthetic implant filler.

A preferred source of keratinous material is human hair, although the keratin may be obtained from hair or fur of animals including any mammal, from finger or toenail material or from hooves, or from the beaks, feet or feathers of birds. Human hair is a preferred source of keratin because of its ready availability from cuttings of barber and beauty shops, because it is expected to be less prone to cause undesirable immune or allergic reactions in a human should any leakage occur, and because a keratin preparation may be made from the hair of a subject for whom the preparation will be used. This last advantage can be especially important in embodiments involving subdermal implantations.

It is well known in the art that keratins are highly sulfated, that is, the amino acid sequence of keratin contains a high proportion of cysteine residues as compared to proteins in general. These cysteines each include a sulfhydryl moiety that is able to bond with another sulfhydril moiety from another cysteine residue to form a disulfide bond known as a cystine residue. The second cysteine may reside within the same keratin molecule, or in another keratin molecule. These disulfide bonds are responsible for much of the tertiary and/or quaternary structure of this class of proteins. A suitable oxidizing agent is able to break this disulfide bond and to oxidize one or both of the sulfide moieties so that they are no longer able to form a disulfide. Such an oxidation is a part of the process of forming the keratin products of the present disclosure. Preferred oxidizing agents include, but are not limited to peracetic acid, hydrogen peroxide, perborates, percarbonates, benzoyl peroxide, or ammonium sulfate peroxide. However, any suitable oxidizing agent known in the art can be used in the practice of the invention. After oxidation, the liquid oxidizing agent can be filtered from the oxidized keratin solid, and the solid may be washed to remove residual oxidizing agent, for example.

The resulting solid may then be suspended in a non-aqueous solvent and the pH may be adjusted upward with base—conveniently to at least neutral pH. Preferred solvents for this second solution do not include significant water as the water may hydrolyze the peptide backbone during processing. Preferred solvents would include alcohols such as methanol, ethanol, or propanol, for example, and would also include non-aqueous solvents such as acetone and tetrahydrofuran, for example. An effective solvent should be able to solvate a base and should also be able to provide a medium able to keep the keratin sufficiently open to allow ionic associations or interactions between the base cations and anionic sulfonic acid groups in the keratin. Preferred bases include, but are not limited to sodium hydroxide, potassium hydroxide and ammonium hydroxide, which, as is known in the art, would yield or produce sodium, potassium and ammonium ions, respectively, upon entering solution.

The keratin suspension may be heated, and is preferably heated to boiling for a time sufficient to swell the keratin. The keratin suspension may be stirred without heat for a longer period of time to allow a more complete association or reaction between the sulfonic acid groups and the base cations. The continued reaction time at or near room temperature, or even below room temperature while stirring is contemplated by the inventors to allow the base cations to approach and bind to the keratin anionic sites with a lower incidence of peptide backbone degradation that could occur with continued boiling. The cations for use in the present invention, therefore, must be able to interact with the anionic cysteic acid groups in the keratin material. The use of the term "cations" or "monovalent cations" in the present disclosure and claims is an indication of those cations that are able to form such an interaction. After a sufficient reaction time, the keratin solid may be removed from the suspension by filtration, for example, and dried, leaving a solid salt formed of the keratin sulfonic acid or cysteic acid groups and base cations. This solid may be shredded into a fibrous form and/or ground into a finely divided powder. This solid may be used in certain embodiments, or it may be hydrated by adding water, for example, and the hydrogel, or viscoelastic hydrogel thus formed may be used in certain embodiments.

The keratin hydrogel so formed is suitable for use as an implant filler, for example, used to fill a breast implant, or to augment soft tissue for cosmetic, reconstructive or aesthetic reasons, or it may be used in a tissue expander. In certain embodiments, a dry keratin hydrogel precursor may be placed in a semipermeable silicone shell, for example and implanted in a body cavity, wound, or scar where new tissue growth is needed. This technique is known in the art to be useful in breast reconstruction, in treatment of male pattern baldness, for treatment of wounds, birth defects, and the like.

The present invention may be described, therefore, in certain aspects as a prosthetic device or implant, or even a tissue expander device, wherein the device includes a composition comprising a hydratable keratin solid to be used as a filler for the device, wherein the solid comprises a keratin where at least a portion of the cysteic groups of the keratin are ionically associated with, or may be ionically bound to cations. As used herein, ionically bound or ionically associated would have their ordinary meaning as is known in the art, and would include the electrostatic attraction between an anion and a cation, and would include such interactions directly, such as through formation of ionic bonds, and interactions through intermediary bipolar moieties, for example. A cysteic group would include cysteine and derivatives of cysteine including cystine and cysteic acid. As used herein, cysteic acid and sulfonic acid denote a cysteine side chain in which the terminal sulfur is bonded to three oxygen atoms to produce the sulfonic acid ion, $SO_3$-, or the acidic form, $SO_3H$. In certain embodiments, a portion of the cysteic groups are oxidized to cysteic acid groups. Cysteic acid groups may comprise a significant portion of the total cysteic groups. The extent of the oxidation may be adjusted by adjusting certain parameters of the oxidation reactions, such as temperature, concentration of oxidizing agent, and time of reaction, for example, to achieve a product with certain desired properties, such as absorbency or resiliency, for example.

In certain embodiments, therefore, the hydratable keratin solid is made by a process comprising oxidizing a portion of the disulfide groups of a keratin to obtain a keratin having oxidized cysteic groups, and contacting the keratin having oxidized cysteic groups with monovalent cations under conditions effective to form ionic associations or ionic bonds between at least a portion of the oxidized cysteic groups and the cations.

In some embodiments, the hydratable keratin solid is made by a process comprising oxidizing at least a portion of the disulfide groups of a keratin to obtain a keratin having oxidized cysteic groups, and contacting said keratin having oxidized cysteic groups with monovalent cations under conditions effective to form ionic associations or ionic bonds between a substantial portion of said oxidized cysteic groups and said cations. The oxidization may comprise placing the keratin in a solution containing a concentration of an oxidizing agent effective to oxidize a portion of the disulfide groups. The portion of oxidized disulfide groups may be a major portion of the total cysteic acid groups.

In certain embodiments of the present invention, the oxidation comprises placing the keratin in a solution containing a concentration of hydrogen peroxide, peracetic acid, perborates, percarbonates, benzoyl peroxide, or ammonium sulfate peroxide effective to oxidize a portion of the disulfide groups.

The process of the present invention may further comprise heating the keratin solid containing oxidized cysteic groups in a solvent solution containing a dissolved base. The solvent solution may comprise a solvent selected from methanol, ethanol, propanol, ether, tetrahydrofuran (THF), and acetone. In certain embodiments the process further comprises removing the solution from the heat and stirring for a time effective to form ionic bonds between the cysteic acid groups and cations produced by the base. The process may also further comprise drying the keratin solid, such as by drying a solid or solution under vacuum.

Another aspect of the present invention includes prosthetic implants that comprise a keratin hydrogel wherein the hydrogel is produced by adding water to a composition comprising a hydratable keratin solid, wherein the solid comprises a keratin where at least a portion of the cysteic acid groups of the keratin are ionically bound to cations. In some embodiments, the hydrogel is a keratin viscoelastic hydrogel produced by adding water to a composition comprising a hydratable keratin solid, wherein the solid comprises a keratin where a portion of the cysteic acid groups of the keratin are ionically bound to or associated with cations.

Another aspect of the present invention is the use in a prosthetic implant of a hydratable keratin solid made by (1) oxidizing keratin in a first solution comprising a soluble oxidizing agent, such that a portion of the disulfide bonds of the keratin are oxidized to form cysteic acid residues, to obtain an oxidized solid fraction; (2) separating the oxidized solid fraction from the first solution; (3) contacting the oxidized solid fraction with a second, basic solution comprising a monovalent cation dissolved in a solvent; (4) maintaining the second solution containing the oxidized solid fraction and the monovalent cations for a time and at a temperature effective to cause an interaction between the cysteic acid residues and the monovalent cations to obtain a salt solution of the keratin and the monovalent cation; and (5) substantially removing the solvent from the salt solution to obtain a hydratable keratin solid.

The process may also further comprise adjusting the pH of the second solution, to obtain a substantially neutral solution. In some embodiments, the keratin is obtained from hair or fur, and is preferably obtained from human hair.

In some embodiments, the keratin is oxidized by suspending the keratin in a solution of a suitable oxidizing agent, such as one selected from the group consisting of hydrogen peroxide, peracetic acid, perborates, percarbonates, benzoyl peroxide, and ammonium sulfate peroxide, in a concentration of between about 1 and about 35 weight/volume percent. In various embodiments, the keratin is oxidized by suspending the keratin in a solution of an oxidizing agent selected from the group consisting of hydrogen peroxide, peracetic acid, perborates, percarbonates, benzoyl peroxide, and ammonium sulfate peroxide, in a concentration of about 1, or about 2, or about 3, or about 4, or about 10, or about 15, or about 20, or about 30, or about 32, or about 35 weight/volume percent. As used herein the term weight/volume percent refers to a solution in which the concentration is determined in weight percent, that is then diluted into a particular volume, arriving at a weight/volume percent. For example, in order to arrive at the oxidant solutions described herein a "stock solution" at fairly high concentration is diluted in water. As an example, hydrogen peroxide may be purchased as a 30 weight % solution (30 grams of peroxide per 100 grams of solution). To make 1 liter of a 2% solution of this, one would dilute 66.7 mL of the 30 weight % stock solution in 933.7 mL of water. The net effect is to cut the stock solution 15-fold (from 30 down to 2%). This ratio is a weight to volume ratio, so the resulting solution is described as 2 weight/volume %.

In some embodiments, the keratin is oxidized by suspending the keratin in a solution of a suitable oxidizing agent, such as one selected from the group consisting of hydrogen peroxide, peracetic acid, perborates, percarbonates, benzoyl peroxide, and ammonium sulfate peroxide, in a concentration of between about 1 and about 35 weight/volume percent, at a temperature between about 0° C. and about 100° C. In other embodiments the temperature is between about 4° C. and about 90° C., or between about 20° C. and about 100° C., or between about 80° C. and about 100° C. In other embodiments, the temperature is about 4° C., or about 90° C., or about 100° C.

The present invention may also include the process wherein the keratin is oxidized by suspending said keratin in a solution of an oxidizing agent selected from the group consisting of hydrogen peroxide, peracetic acid, perborates, percarbonates, benzoyl peroxide, and ammonium sulfate peroxide, in a concentration of between about 1 and about 35 weight/volume percent, at a temperature between about 0° C. and about 100° C. for a period of between 0.5 and about 24 hours, or in a concentration of oxidizing agent of between about 1 and about 35 weight/volume percent, at a temperature between about 0° C. and about 100° C. for a period of between 1 and about 2 hours, or for between about 2 and about 4 hours, or for between about 1 and about 4 hours, or for a period of about 10 hours.

More specifically, the process of making the keratin solid may include oxidizing the keratin by suspending the keratin in a solution of between about 1 percent to about 32 percent peracetic acid at a temperature between about 0° C. and about 100° C. for between about 0.5 and about 24 hours, or by suspending the keratin in a solution of about 1 percent peracetic acid at a temperature between about 0° C. and about 100° C. for between about 0.5 and about 24 hours, or by suspending the keratin in a solution of between about 4 percent peracetic acid at a temperature of about 4° C. for 24 hours, or by suspending the keratin in a solution of about 4 percent peracetic acid at room temperature for about 24 hours, or by suspending the keratin in a solution of about 4 percent peracetic acid at about 90° C. for about 10 hours, or by suspending the keratin in a solution of about 4 percent peracetic acid at a temperature between about 20° C. and about 100° C. for between about 1 and about 4 hours, or by suspending the keratin in a solution of about 4 percent peracetic acid at a temperature between about 80° C. and about 100° C. for between about 1 and about 2 hours, or even by suspending the keratin in a solution of about 2 percent peracetic acid at a temperature between about 0° C. and about 100° C. for about 2 hours.

A second solution in the process of making the disclosed keratin compositions, wherein the second solution contains the oxidized solid fraction and monovalent cations may be heated, and may also be boiled for between about 0.5 hours and about 12 hours, for between about 0.5 hours and about 3 hours, or for about 1 hour. When said solution is boiled, the solution may be allowed to continue reacting while being stirred after removal of the heat. Alternatively, the solution may be stirred and allowed to react without the application of heat, or of boiling temperatures. In certain embodiments, the solution is allowed to react at a temperature of between about 15° C. and about 30° C. for a period of between about 1 and about 24 hours, or at a temperature of between about 20° C. and about 25° C. for a period of between about 1 and about 5 hours, or at room temperature for a period of about 5 hours.

Implants made with a hydratable keratin solid offer particular advantages over other implants, especially in implants that involve a large amount of material, such as breast or gluteal pad implants. In a preferred method of use, the hydratable keratin solid in powder or fiber form may be added to an envelope interior prior to insertion, and water may then be injected into the envelope after implantation, thus forming the hydrogel in situ. In the practice of this embodiment, the implant envelope containing a dry solid will have a small volume relative to the size of the final implant, thereby allowing a relatively small incision for insertion of the implant. In certain applications, it may be more advantageous to implant an empty envelope, again allowing for a relatively small incision, to form a hydrogel outside the body and then injecting the hydrogel into the envelope through a large bore needle, for example. It is also understood that implants may be formed with the hydrogel in place in the envelope prior to implantation.

Tissue expanders made with a hydratable keratin solid offer particular advantages over other tissue expanders, especially tissue expanders which require volume adjustments which are made through an externally filled tube. The use of an external filling is often uncomfortable and inconvenient for the patient, and can lead to an increased incidence of infection. In a preferred method of use, the hydratable keratin solid in powder or fiber form may be added to a tissue expander envelope interior. The permeation of body fluids through the envelope can be controlled through the use of certain materials and engineering principle well known to those skilled in the art. The control of the diffusion rate has the effect of controlling the hydration rate of the keratin solid and thus, the expansion rate of the hydrogel thus formed. The expansion rate can thus be controlled in-situ, without the use of an external fill tube. This method of use would lead to a more comfortable and convenient tissue expander with lower incidence of infection. Alternatively, the hydration rate of the keratin solid can be controlled by controlling the absorbency of the keratin solid during manufacture as described herein. A solid tissue expander formed from an absorbent keratin solid with a controlled absorption rate would have the advantage of expanding its volume at a controlled rate in-situ, and thus providing the same advantages as noted previously.

In certain embodiments implants can be made using a keratin hydrogel formed using a method that does not include a hydratable keratin solid stage. An implantable keratin hydrogel can be made by a process beginning with providing a keratinous material from a biological source, such as hair, fur, feathers, hooves or nails, most preferably human hair, and oxidizing the hair or other keratin material. The oxidized hair can be suspended in a base solution, such as an ammonium hydroxide solution, for example, wherein the solution contains thioglycolate. The solution may then be heated, and stirred under an inert environment such as an $N_2$ environment, for example. Although the use of a nitrogen environment may be preferred for certain embodiments, any oxidatively inert gas such as argon or helium, for example, may also be used. A swelled fraction of keratin gel can be separated from the suspension and added to an oxidizing agent such as hydrogen peroxide or peracetic acid, for example. Alternately, the swelled fraction can be exposed to ambient air. The gel can be allowed to stand in the oxidizing environment, thereby forming a crosslinked hydrogel. This method of forming a crosslinked gel is described more completely in U.S. Pat. No. 5,932,552 incorporated herein by reference.

The implant can be made by filling the envelope interior either before or after implantation. In implants filled after implantation, the implant can be rolled into a small profile shape and inserted through a small incision into the interior of a breast or other organ or area to receive an implant. As is well known in the art, an incision for breast replacement may be made in the navel, or near the edge of a mastectomy scar, for example, and incisions for augmentation may also be made in the crease at the bottom of the breast or around the areolar area of the breast. The envelope can then be unrolled and the hydrogel injected through a large bore needle, using the same incision used to insert the envelope. The injection can be made into a self-sealing port provided in the envelope.

Hair is a preferred source of keratin for the present invention. In particular, human hair is a preferred source. In one method, hair is harvested from the intended implant recipient. While any human hair is believed suitable as a source, the use of hair from the intended recipient may provide a psychological and allergenic advantage relative to hair from other sources.

DETAILED DESCRIPTION OF THE INVENTION

The present invention arises from the discovery by the present inventors that prosthetic implants, or implants to replace or augment soft tissues in the body, especially in the human body can be made from a keratin material, and in a most preferred embodiment, from human hair. The implants described herein offer numerous advantages over other implants, especially silicone, saline, or even autogenous fat cells. These advantages include that the keratin gel implants are less toxic than silicone implants should a leakage occur, keratin gel implants have a more natural look and feel than saline implants, and keratin implants require an incision or injection only at the site of implant, and do not require a second invasive procedure for harvesting tissue such as fat cells, for example.

EXAMPLE 1

Implants Utilizing Keratin Hydrogel from Solid Precursor

The present example describes implants having a keratin hydrogel contained within an envelope, where the keratin hydrogel is formed from a solid, keratin hydrogel precursor which forms a keratin hydrogel upon the addition of water. The solid precursor form of keratin derived implant material may be used in several ways, depending on the need of the practitioner. For example, the solid may be hydrated prior to placing the keratin filler into an implant envelope. In the practice of this method, one would be able to determine precisely the volume of the implant filler prior to placing the filler in the envelope of the implant. The hydrated gel could then be injected into the envelope either before or after the envelope is implanted. It is understood that the invention would include prepackaged, sterile, prefilled, sealed implants as well as a package that includes various sized envelopes and a separately packaged hydrogel, or hydrogel precursor.

In certain embodiments, a solid precursor may be added directly to an implant envelope and subsequently hydrated in the envelope either before or after the envelope is implanted. Again, hydrating the keratin after implantation, or injecting the hydrated gel into the envelope after implantation both allow a much smaller incision to be made, and allow the injection through the same incision of either water or hydrogel. This embodiment of the invention would include a packaged implant with a premeasured amount of solid hydrogel precursor, or would include the separate packaging of envelopes and solid precursor.

In the present example, a solid hydrogel precursor can include protein having an ionizable pendant group, such as sulfonic acid, or cysteic acid, which can be derived from an oxidized protein disulfide linkage. A preferred source of protein is keratin, preferably keratin obtained from hair, and most preferably keratin obtained from human hair. While hair is a preferred source of keratinous material, other keratinous materials are also believed suitable for use in the present invention. Examples of other sources include animal hair or fur, skin, hooves, feathers, beaks, feet and horns. The patient or a human donor are some preferred sources of hair, as hair from these sources is most likely to result in a non-antigenic product, although animal hair may be acceptable for many individuals. In one method according to the present invention, hair is provided, preferably clean and unbleached. In another method, the hair is washed with Versa-Clean™ (Fisher Scientific, Pittsburgh, Pa.), or other cleaners, rinsed with deionized water, and allowed to dry.

In a preferred method of preparing a solid hydrogel precursor, cleaned hair can be oxidized in peracetic acid or another suitable reagent such as $H_2O_2$. One method utilizes between about 1% to 32% peracetic acid, at a temperature between about 0 degrees C. and 100 degrees C. for between 0.5 and 24 hours. In one method, about 1 weight/volume percent peracetic acid is used. One method treats 30 grams of hair with 500 mL of 4% peracetic acid at 4 degrees C. for 21 hours. Another method treats the hair at room temperature for 24 hours. Yet another method treats the hair at about 90 degrees C. for about 10 hours. In a preferred method, the hair is treated by heating the hair in the oxidizing agent for between about 1 and 4 hours at a temperature between about 20 and 100 degrees C. In a more preferred method, the hair is treated by heating the hair in the oxidizing agent for between about 1 and 2 hours at a temperature between about 80 and 100 degrees C. In a most preferred method, the hair is treated by heating the hair in about 2 weight/volume percent oxidizing agent for about 2 hours at a temperature of about 100 degrees C. The oxidation is believed to cleave a significant portion of keratin disulfide bonds forming cysteic acid residues. The sulfonic acid groups are believed to be hydrophilic in nature and will ionically bond to cations later in the process, forming a salt of the keratin and cation.

After oxidation, the keratin solid can be recovered from the oxidizing liquid using filtration or other suitable methods such as centrifugation or decantation. The recovered, oxidized solid may be washed with water or any other suitable liquid such as an alcohol, including methanol or ethanol, for example, to remove the excess oxidizing agent.

The solid fraction can be suspended in a suitable solvent. The solvent should be capable of at least suspending the hair or keratin solid and keeping the solid sufficiently swelled for subsequent reaction. The solvent is preferably a non-aqueous solvent, as the presence of water can contribute to hydrolysis of peptide backbone bonds of the protein product, which can result in an inferior product. The solvent should also be able to solubilize the later added cation. One group of suitable solvents includes alcohols such as methanol and ethanol. Other solvents such as ether, tetrahydrofuran (THF), and acetone may also be suitable as solvents. The solvent used is preferably volatile to promote evaporation from the final solid product.

The hair or keratin solvent suspension may then have the pH titrated upward to at least about pH 7, or preferably to a pH at or above the pKa of the sulfonic acid groups of the protein. This increased pH acts to ionize or deprotonate the sulfonic acid groups and allows ionic interactions with cations. The cations are preferably produced by including a base in the solution, preferably a monovalent base, or a base that provides a monovalent cation in solution. Preferred bases include, but are not limited to ammonium hydroxide, sodium hydroxide and potassium hydroxide.

The keratin suspension can be heated for a time and temperature sufficient to swell the keratin structure and promote neutralizing of the sulfonic acid sites with the provided cation. In a preferred method, the keratin is suspended in ethanol and boiled between about 0.5 hours and 12 hours in the presence of the cation. More preferably, the keratin is suspended in ethanol and boiled between about 0.5 hours and 3 hours in the presence of the cation. In one method, the keratin is suspended in ethanol and boiled for about 1 hour in the presence of the cation. Boiling for too long a time period is believed to lead to a final, partially solubilized or mushy keratin which may result from degradation of the peptide backbone. A partially solubilized keratin product is less preferred due to the greater difficulty of grinding the keratin.

After boiling, the keratin is preferably allowed to continue to react with the provided base cations at lower temperature and with stirring. The lower temperature reaction preferably takes place at a temperature of between about 15 and 30 degrees C. for between about 1 and 24 hours. More preferably, the lower temperature reaction takes place at a temperature of between about 20 and 25 degrees C. for between about 1 and 5 hours. In one method, the keratin suspension is allowed to react with stirring at room temperature for about 5 hours.

After ion exchange at lower temperature, the solid salt can be separated from the solvent using any suitable method such as filtration. The solid is preferably washed with a solvent that may be the same solvent as that used in the reaction. Washing the keratin removes excess base, which is preferably removed to make the keratin solid neutral.

After filtration and washing, the keratin can be dried by a method such as evaporation under vacuum. In one method, the keratin is dried at room temperature under about 5 mm Hg vacuum for about 2 hours. The dried keratin is preferably somewhat brittle, which can result in a better product after grinding. The dried keratin can be shredded into fibers or can further be ground into a powder. The dried keratin can be directly ground into a powder using a mortar and pestle, a ball mill, or other means of breaking down or comminuting the dried keratin into particles. Solid keratin hydrogel precursor can be provided in either fibrous or powder form for use in the implant.

The solid keratin hydrogel precursor is capable of absorbing many times its own weight in water. In one test, fibers were shown to absorb an average of 13 times their weight in water at 21.5° C., and may absorb up to 20 times. The absorbed water is chemically bound to the keratin through acid-base interactions such as hydrogen bonding. This results in a stable, viscoelastic hydrogel from which the water cannot be separated by normal mechanical means such as centrifugation or compression.

A patient, the intended recipient, can be prepared for the operation and a small incision made at the breast or other area to receive an implant. The envelope can be rolled into a cylinder or other small shape to decrease the profile and the compacted envelope inserted through the incision. The envelope can be allowed to attain a less constrained shape well known to those skilled in the art, such as a meniscus or soft disc shape. Leaving the envelope empty or containing only a solid hydrogel precursor can greatly decrease the volume of the envelope during insertion. Decreasing the volume can greatly decrease the implant profile and the required incision size. By waiting to inject any fluid into the implant until after implantation, a more minimally invasive procedure can be performed. In one method, the envelope includes a self-sealing injection port in the envelope wall. A large hypodermic syringe can be used to inject the fluid into the self-sealing port. The large hypodermic is preferably inserted through the already formed incision in the breast or other tissue, to avoid the need for an additional puncture. In embodiments having a keratin hydrogel precursor in the envelope, the injected fluid can be water, thus forming the hydrogel in situ. In embodiments using a preformed hydrogel, the hydrogel can be injected through a preferably large bore needle and into the envelope interior. While the hydrogel can be quite viscous, the needle bore can approach the size of the incision in some embodiments. After implantation, the incision can be closed and allowed to heal.

EXAMPLE 2

Tissue Expanders Utilizing Keratin Hydrogel from Solid Precursor

The present example describes tissue expanders having a keratin hydrogel contained within an envelope, where the keratin hydrogel is formed from a solid, keratin hydrogel precursor which forms a keratin hydrogel upon absorption of body fluids. A variety of different sized tissue expanders can be provided by varying the size of the envelope and the amount of keratin hydrogel precursor. In addition, the rate at which the tissue expanders reached their final volume can be varied by controlling the diffusion rate of body fluids into the tissue expander, or by varying the absorbency of the dry keratin solid, as described herein.

A patient, the intended recipient, can be prepared for the operation and a small incision made in or near the breast or other area to receive a tissue expander. Placing the tissue expander in its dehydrated form allows for the implant to absorb body fluids through the envelope at a controlled rate, thus increasing in volume at a controlled rate. The volume expansion occurs in-situ, after the incision has been closed, and provides a more comfortable and convenient implant when compared to conventional treatments. A lower incidence of infection would result from having a closed incision without the need for an external fill tube as in conventional tissue expander products.

EXAMPLE 3

Implants Using Keratin Hydrogel Formed From Keratin With Added Hydrophilic Groups and With Reformed Crosslinks In the present example, an alternate embodiment is described, a keratin hydrogel that is provided using a method that does not involve adding water to a solid keratin hydrogel precursor. The keratin material may be obtained from the same sources as described in Example 1, and preferred source of keratin is human hair. In one method, hair is provided, preferably washed and unbleached. The hair is harvested from a human or animal source. The patient or another human donor is a preferred source of hair, as hair from these sources is most likely to result in a non-antigenic product, although animal hair may be acceptable for certain individuals that do not have animal product allergy problems. In one method, the hair is washed with Versa-Clean™ (Fisher Scientific, Pittsburgh, Pa.) or other suitable cleansing agent, rinsed with deionized water, and allowed to air dry.

The hair can be oxidized in peracetic acid or another suitable reagent such as $H_2O_2$-A preferable treatment utilizes from 1% to 32% peracetic acid, at a temperature between about 0 degrees C. and 100 degrees C. for between 0.5 and 24 hours. One method treats 30 grams of hair with 500 mL of 32% peracetic acid at 4 degrees C. for 24 hours. This treatment with peracetic acid is believed to partially oxidize the naturally occurring disulfide linkages to produce a protein with cysteic acid (—$CH_2SO_3H$) residues.

The hair is recovered, preferably with filtration through a coarse fritted glass filter, and rinsed numerous times with deionized water until the rinse solution has a pH of 6.0 or higher. The hair can then be dried in a vacuum oven at between 20 degrees C. and 50 degrees C. for between 0.5 and 5 days. One method dries the hair in a vacuum oven at 40 degrees C. for several days. The dried hair can then be pulverized and ground into a fine powder. One method of grinding the hair uses a ceramic mortar and pestle.

The keratin powder can be suspended in a sulfhydryl solution such as an ammonium thioglycolate solution, for example. In one method, pulverized keratin powder, derived from hair as described above, is suspended in about 3N ammonium hydroxide containing thioglycolate. About six grams of keratin powder can be added per 75 mL of 3N ammonium hydroxide solution. The strength of ammonium hydroxide is preferably about 3N and the preferred concentration of ammonium thioglycolate is from about 2 to about 20 ml (as thioglycollic acid) per 75 ml of ammonium hydroxide, or about 11 ml thioglycolate per 75 ml ammonium hydroxide in certain embodiments. The suspension can then be heated for a time sufficient to solubilize the soluble fraction of the hair. The suspension in one method is heated to between 50 degrees C. and 90 degrees C. for between 1 and 24 hours, followed by cooling. In a preferred method, the suspension is heated to about 60 degrees C. for about 4 hours and cooled to room temperature.

Applicants believe this treatment cleaves the remaining disulfide linkages to produce cysteine residues in the protein structure. At this point, the keratin protein is believed to contain sulfonic acid, sulfhydril and cystine-thioglycolate containing residues. The ratio of sulfonic acid residues and sulfhydril residues can be controlled by varying the time, temperature, and concentration of oxidant in the peracetic acid treatment step previously described. The presence of sulfonic acid residues imparts a hydrophilic property to the hair as well as to the final hydrogel product.

After the treatment described above, a keratin fraction resistant to the treatment remains, consisting primarily of beta keratin. This fraction is insoluble in the suspension and is removed in one method by centrifugation at about 10,000 g for about 10 minutes. The insoluble fraction is set aside and is available for other uses. A thick, jelly-like supernatant remains which includes a soluble keratin fraction. The supernatant is collected and used to make the implant material described herein.

The supernatant is preferably purified, using a method such as dialysis. A preferred method uses dialysis against running water using a dialysis membrane (Spectra/Por™) having a cutoff of about 8000 MW. The resulting solution is preferably concentrated to a concentration of about 0.1 grams per mL.

The keratin in solution is now ready for crosslinking to form a hydrogel. In a preferred method, an oxidizing agent is added to the keratin to crosslink the keratin proteins. Preferred oxidizing agents include oxygen, hydrogen peroxide, organic peracids, peroxy carbonates, ammonium sulfate peroxide, benzoyl peroxide, and perborates. Hydrogen peroxide is preferably added to the keratin solution at about 0.5% to about 1.0% w/v, mixed well, and allowed to stand at room temperature for several days. A preferred standing time is about 3 days. The freely flowing solution slowly thickens and converts to a crosslinked hydrogel after about 72 hours.

The insoluble keratin fraction from hair is thus partially oxidized so as to have the protein backbones interconnected with disulfide linkages and having sulfonic acid residues. The partially oxidized keratin is treated with a reducing agent to cleave some or all of the remaining disulfide bonds, forming thiol groups and cystine-thioglycolate groups and solubilize more of the keratin proteins. After removing the insoluble fraction, the keratin is oxidized to allow the formation of disulfide crosslinks. Disulfide crosslinks are thus reformed. As used herein, the term "reformed" refers to crosslinks broken and formed later in time, where individual linkages later formed could be, but are not necessarily, between the same amino acid cysteine pairs.

A crosslinked, pure keratin hydrogel results. The hydrogel has sulfonic acid groups which are hydrophilic and bind water within the hydrogel. The number of sulfonic acid groups corresponds to the degree of keratin oxidation in the partial oxidation step.

In one method for implanting the envelope, the hydrogel is formed by adding the oxidizing agent to the keratin supernatant outside of the envelope followed by mixing. After a time period, the mixed hydrogel and oxidizing agent or other crosslinking agent can be injected into the implant envelope. In some procedures, the envelopes are prefilled with keratin hydrogel prior to packaging the implant. In some procedures, the envelopes are filled with keratin hydrogel by injection only after implantation of the envelopes. In some procedures, the oxidizing agent and keratin supernatant are mixed close to the time of the surgical procedure, and the mixture injected soon after mixing, before the mixture becomes very viscous. In these procedures, the mixture can be allowed to thicken in situ.

The present invention includes hollow implants which can have a thicker envelope wall than those commonly used in breast implants. A keratin hydrogel can be used to fill any hollow implant envelopes known in the art, including penile implants, testicular implants, chin implants, intervertebral disk implants, and gluteal pad implants.

Numerous advantages of the invention covered by this disclosure have been set forth in the foregoing description. It will be understood, however, that this disclosure is, in many respects, only illustrative. Changes may be made in details, particularly in matters of substitutions of chemically or biologically equivalent substances, or in the order of steps in certain methods without exceeding the scope of the invention. The invention's scope is, of course, defined in the language in which the appended claims are expressed.

What is claimed is:

1. An intervertebral disk implant comprising:
   an envelope; and
   a keratin hydrogel within said envelope;
   wherein the keratin hydrogel is formed of keratin in which the cysteine amino acids are free of extrinsic chemical groups added by reduction of cystine disulfide bonds.

2. The intervertebral disk implant of claim 1 wherein:
   said envelope is comprised of one of silicone, and a biocompatible polymer.

3. The intervertebral disk implant of claim 1 wherein:
   said envelope has a self-sealing port.

4. A medical package for use as an intervertebral disk implant, wherein said package comprises a formulation comprising a keratin hydrogel wherein the keratin hydrogel is formed of keratin in which the cysteine amino acids are free of extrinsic chemical groups added by reduction of cystine disulfide bonds.

5. The intervertebral disk implant of claim 4 wherein:
   said package includes an envelope that is comprised of one of silicone, and a biocompatible polymer.

6. The intervertebral disk implant of claim 4 wherein:
   said package includes an envelope that has a self-sealing port.

7. A method for implanting a prosthetic intervertebral disk comprising the steps of:
   selecting an envelope containing a keratin hydrogel;
   accessing the intervertebral space adjacent a vertebra; and
   implanting the envelope into the space
   wherein the keratin hydrogel is formed of keratin in which the cysteine amino acids are free of extrinsic chemical groups added by reduction of cystine disulfide bonds.

8. A method for implanting a prosthetic intervertebral disk comprising the steps of:
   selecting an envelope with an interior;
   selecting a keratin hydrogel wherein the keratin hydrogel is formed of keratin in which the cysteine amino acids are free of extrinsic chemical groups added by reduction of cystine disulfide bonds;
   accessing the intervertebral space between adjacent vertebra;
   implanting the envelope into the intervertebral space; and
   introducing the keratin hydrogel into the interior of the envelope.

9. A method for implanting a prosthetic intervertebral disk comprising the steps of:
   harvesting hair from a patient;
   having the hair processed into a keratin hydrogel wherein the keratin hydrogel is formed of keratin in which the cysteine amino acids are free of extrinsic chemical groups added by reduction of cystine disulfide bonds;
   selecting an envelope having an interior;
   accessing the intervertebral space between adjacent vertebra;
   implanting the envelope into the intervertebral space; and
   introducing the keratin hydrogel into the interior of the envelope.

10. A method for implanting a prosthetic intervertebral disk comprising the steps of:
    selecting an envelope;
    accessing the intervertebral space between adjacent vertebra;
    implanting the envelope into the space; and
    introducing a keratin hydrogel into the envelope
    wherein the keratin hydrogel is formed of keratin in which the cysteine amino acids are free of extrinsic chemical groups added by reduction of cystine disulfide bonds.

11. A method for making a prosthetic intervertebral disk kit for a patient comprising the steps of:
    selecting an envelope having an interior capable of containing a gel;
    having human hair harvested; and
    processing the hair into a keratin hydrogel
    wherein the keratin hydrogel is formed of keratin in which the cysteine amino acids are free of extrinsic chemical groups added by reduction of cystine disulfide bonds.

12. The method of claim 8 wherein said selecting step includes:
    selecting an envelope provided in a low profile shape.

13. The method of claim 8 wherein said selecting step includes;
   selecting an envelope provided in a rolled up shape.
14. The method of claim 9 wherein said selecting step includes:
   selecting an envelope provided in a low profile shape.
15. The method of claim 9 wherein said selecting step includes;
   selecting an envelope provided in a rolled up shape.
16. The method of claim 10 wherein said selecting step includes:
   selecting an envelope provided in a low profile shape.
17. The method of claim 10 wherein said selecting step includes;
   selecting an envelope provided in a rolled up shape.
18. The method of claim 11 wherein said selecting step includes:
   selecting an envelope provided in a low profile shape.
19. The method of claim 11 wherein said selecting step includes;
   selecting an envelope provided in a rolled up shape.
20. The method of claim 12 including after the implanting step, the step of unrolling the envelope.
21. The method of claim 13 including after the implanting step, the step of unrolling the envelope.
22. The method of claim 14 including after the implanting step, the step of unrolling the envelope.
23. The method of claim 15 including after the implanting step, the step of unrolling the envelope.
24. The method of claim 16 including after the implanting step, the step of unrolling the envelope.
25. The method of claim 17 including after the implanting step, the step of unrolling the envelope.
26. In an intervertebral disk implant, the improvement comprising:
   a keratinous gel
   wherein the keratinous gel is a keratin hydrogel formed of keratin in which the cysteine amino acids are free of extrinsic chemical groups added by reduction of cystine disulfide bonds.
27. In a method for implanting a prosthetic intervertebral disk, the improvement comprising the steps of:
   selecting a keratin hydrogel wherein the keratin hydrogel is formed of keratin in which the cysteine amino acids are free of extrinsic chemical groups added by reduction of cystine disulfide bonds;
   accessing the intervertebral space between adjacent vertebra; and
   implanting the keratin hydrogel into the space.
28. An intervertebral disk implant comprising:
   a keratinous gel
   wherein the keratinous gel is a keratin hydrogel formed of keratin in which the cysteine amino acids are free of extrinsic chemical groups added by reduction of cystine disulfide bonds.
29. A method for implanting a prosthetic intervertebral disk comprising the steps of:
   selecting a keratin hydrogel wherein the keratin hydrogel is formed of keratin in which the cysteine amino acids are free of extrinsic chemical groups added by reduction of cystine disulfide bonds;
   accessing the intervertebral space between adjacent vertebra; and
   implanting the keratin hydrogel into the space.

* * * * *